United States Patent [19]
Kojima et al.

[11] Patent Number: 6,093,850
[45] Date of Patent: Jul. 25, 2000

[54] PROCESS FOR THE SYNTHESIS OF UREA AND EQUIPMENT THEREFOR

[75] Inventors: Yasuhiko Kojima; Hidetsugu Fujii, both of Chiba, Japan

[73] Assignee: Toyo Engineering Corporation, Tokyo, Japan

[21] Appl. No.: 09/269,164

[22] PCT Filed: Dec. 17, 1998

[86] PCT No.: PCT/JP98/05698

§ 371 Date: Mar. 23, 1999

§ 102(e) Date: Mar. 23, 1999

[87] PCT Pub. No.: WO99/31053

PCT Pub. Date: Jun. 24, 1999

[30] Foreign Application Priority Data

Dec. 18, 1997 [JP] Japan .................................. 9-349340

[51] Int. Cl.$^7$ ................................................. C07C 273/04
[52] U.S. Cl. ............................... 564/68; 564/67; 564/69; 564/70; 564/71; 564/72
[58] Field of Search ................................. 561/67, 68, 69, 561/70, 71, 72

[56] References Cited

U.S. PATENT DOCUMENTS 3,720,548  3/1973  Barake et al. ..................... 148/6.14 R

*Primary Examiner*—Peter O'Sullivan
*Attorney, Agent, or Firm*—Oblon, Spivak, McClelland, Maier & Neustadt, P.C.

[57] ABSTRACT

The present invention provides an improved process for synthesizing urea from ammonia and carbon dioxide while preventing corrosion of sites, that are to be in contact with a condensate, of the joints of a tube plate and cooling tubes in a condenser installed vertically or horizontally. According to this process, the sites, that are to be in contact with the condensate, of the joints of the tube plate and the cooling tubes in the condenser are prevented from corrosion by enveloping the sites with liquid ammonia or a solution rich in ammonia in the synthesis of urea comprising separating unreacted ammonia and carbon dioxide as a gaseous mixture thereof from a urea synthesis solution at a pressure substantially equal to the urea synthesis pressure, bringing the gaseous mixture into contact with an absorption medium in the condenser to form a condensate, and recirculating the condensate to the synthesis column.

8 Claims, 4 Drawing Sheets

PROCESS FOR THE SYNTHESIS OF UREA AND EQUIPMENT THEREFOR

This application is a 371 of PCT/JP98/05698 filed Dec. 17, 1998.

TECHNICAL FIELD

This invention relates to an improvement in an urea synthesis process in which unreacted ammonia and carbon dioxide contained in the urea synthesis solution are separated as a gaseous mixture of ammonia, carbon dioxide and water at a pressure substantially equal to the urea synthesis pressure, the gaseous mixture is condensed under cooling in a condenser having a multi-tubular cooler, and the condensate thus-obtained is recycled to the urea synthesis.

BACKGROUND ART

Urea synthesis processes, which comprise reacting ammonia and carbon dioxide in an urea synthesis column at a urea synthesis pressure and a urea synthesis temperature, separating ammonium carbamate from the thus-obtained urea synthesis solution at a pressure substantially equal to the urea synthesis pressure as a gaseous mixture of ammonia and carbon dioxide, causing an absorption medium to absorb said gaseous mixture so as to recycle the absorbed medium to the urea synthesis column, and separately providing an urea solution from the urea synthesis solution from which said ammonium carbamate has been separated, are well known, and a variety of proposals have been made with regard to the processes. In the processes, since liquid is allowed to flow down from the condenser to the urea synthesis column and from the urea synthesis column to the stripper by head difference, it is necessary to place the condenser and urea synthesis column at high grounds.

It is well known that the above-described processes employ corrosion-preventive oxygen supplied to the urea synthesis column, condenser and stripper as a countermeasure to corrosion. The oxygen, being dissolved in the urea synthesis solution, is supplied onto anticorrosive films in the interior of the equipments, and therefore the interior of the equipments was protected from corrosion.

As described above, even if the interior was immersed in a highly corrosive recovery solution or urea synthesis solution, corrosion prevention was possible as far as corrosion-preventive oxygen was supplied, although it depended on the operating pressure and temperature, liquid conditions and other conditions.

By reasons of much time and labor taken to install and repair the equipments, there have been developed urea synthesis processes wherein urea synthesis column and other equipments are placed on the ground.

The applicant previously proposed, in Japanese Patent Application No. 234364/1997, a urea synthesis process which permits placing the synthesis column and other equipments on the ground.

The proposal relates to a urea synthesis process and an apparatus therefor in which a urea synthesis column is installed in a lower part and a vertical condenser is installed thereon or thereabove, a first downpipe is provided to make the condenser communicate with the urea synthesis zone, the condensate is allowed to flow down by gravity from the top part of the condenser through the down pipe to the bottom part of the urea synthesis zone, and the condensate thus having flowed down is allowed to flow down by gravity through a second down pipe having an opening in the top part of the urea synthesis column to the top part of a stripper, or to a process in which the condensate from a vertical condenser is sucked by an ejector using heated feed liquid ammonia as a driving fluid and introduced into the bottom part of the urea synthesis column where it is subjected to urea synthesis, and an apparatus therefor.

In the above processes, a recovery solution is supplied to the shellside of the condenser. The operating conditions in the condenser in the former process are such that the pressure is the same as that of the urea synthesis, the molar ratio of ammonia to carbon dioxide (referred to as N/C hereunder) is controlled at 2.5–4.5, the molar ratio of water to carbon dioxide (referred to as H/C hereunder) at 0.0–1.0, the residence time at 10–30 minutes, and the operating temperature is controlled to be 170–190° C., so that a urea synthesis rate of 20–60% is achieved.

In the latter process, the pressure is selected from 140–250 bar, the N/C is set at 2.5–3.5, the H/C at 0.0–1.0, the residence time at 10–30 minutes, and the operating temperature is controlled to be 130–250° C., preferably 170–190° C., so that a urea synthesis rate of 20–60% is achieved.

Another example suggesting to place equipments on the ground includes a urea production process disclosed in Japanese Patent Laid-Open Publication No. 209555/1985. The publication discloses that condensation in the condensing zone is carried out in an immersed condenser, particularly, in the shellside of a tubular heat exchanger arranged horizontally and also that the condensation can be effected in a condensing zone integrated with a reaction zone. According to the publication, in the condensing zone, the pressure is selected from 125–350 bar which are equivalent to the synthesis pressures, and at least 30% of the achievable equilibrium amount of urea is formed. These descriptions and examples teach that the operating temperature is 130–150° C.

In the foregoing prior art, it is possible to synthesize urea in the shellside of the condenser. In any case, regardless of whether the condenser is installed vertically or horizontally, a tube plate and cooling tubes in the condensing zone are immersed in a highly corrosive solution comprising ammonia, ammonium carbamate, urea and water in the foregoing prior art. The condenser is in the conditions of pressure and temperature capable of synthesizing urea and therefore is under an environment where below-described crevice corrosion and corrosion of joints including weld joints of the tube plate and the cooling tubes were apt to take place.

As it is well known, the condenser has hundreds to a thousand or more of cooling tubes installed therein, although the number varies with production. Therefore, when below-described troubles occurred, it took much time and effort to discover the trouble spots. Further, when one tried to repair the trouble spots during peridic maintenance, it was practically impossible to repair them from the shellside, because there was no space available for men to enter the equipment and repair the spots.

As described above, the condenser has cooling tubes installed in a tube plate, and as one of the installation methods, there is mentioned a tube expansion method or a method in which tube expansion and sealweld with tube plate are combined. In these methods, it is well known that minute crevices evolve between the tube plate and the cooling tubes upon fabrication. When a recovery solution or urea synthesis solution creeps into the crevices, the solution remains in the crevices. Under such conditions, corrosion-preventive oxygen supplied to the aforesaid anticorrosive films is deficient. As a result, an environment is formed where corrosion called crevice corrosion is liable to occur between the tube plate and the tubes, and troubles are caused such that part of the cooling tubes are broken or the tube plate is damaged by corrosion.

When part of the cooling tubes were broken, there was no particularly effective countermeasure other than filling plugs in the broken tubes to stop the cooling functions of the tubes. Especially, when the tube plate was damaged by corrosion, no repairing method could be applied.

In view of the above circumstances, as one of the methods for avoiding crevice corrosion, a method has been practiced wherein a tube plate is directly welded to cooling tubes by internal bore welding or internal bore butt welding (hereinafter referred to as internal bore welding). However, under the operating conditions of a pressure of 150–300 bar and a temperature of 150–200° C. in the condenser, the weld joints are immersed at all times in a highly corrosive recovery solution and joined solution thereof with the condensate and subjected also to heat history. Accordingly, since these factors are entwined with each other complicately, it has been impossible to prevent completely troubles, such as crack of the weld joints due to heat history, corrosion due to the highly corrosive recovery solution, and compounded crack and corrosion due to heat history and the recovery solution.

When such troubles occurred, there was no practically effective countermeasure except for stopping operation for a while and filling plugs in the damaged cooling tubes to suspend the function of the tubes.

Even when plugs are struck in, wetting of the weld joints is not avoided and the synthesis solution stays in the plug-struck cooling tubes without being replaced, so that corrosion of the tubes increases acceleratingly due to deficiency of dissolved oxygen and even the plugs themselves may also be corroded eventually.

Even if the corresponding spots were rewelded during periodic maintenance, its preparation took much time and costed a great deal, so that this way of maintenance was not so advantageous.

As has been described above, it has been expectd to propose means for preventing troubles such as crack and corrosion of the joints of a tube plate and cooling tubes and of the internal bore weld joints of a tube plate and cooling tubes regardless of in the synthesis column or in the condenser, and a process for synthesizing urea using said means.

DISCLOSURE OF THE INVENTION

It is an object of the present invention to provide a process for synthesizing urea, which has a means for preventing troubles such as crack and corrosion of the joints of a tube plate and cooling tubes and the internal bore weld joints of a tube plate and cooling tubes.

The present inventors have found that when placed in an environment rich in ammonia that is extremely less corrosive, weld joints subjected to the aforesaid crevice corrosion and heat history at a urea synthesis pressure of 150–300 bar and a synthesis temperature of 150–200° C. hardly suffer cracking and corrosion. As a result of intensive investigation, the present invention has been completed.

The present invention has been made on the basis of the aforesaid circumstances and findings. Consequently, the aforesaid object of the present invention can be achieved by the process for synthesizing urea and apparatus therefor set forth below.

An improved process for synthesizing urea comprising reacting ammonia with carbon dioxide at a urea synthesis temperature and a urea synthesis pressure in a urea synthesis column, heating the resultant urea synthesis solution comprising urea, unreacted ammonia, unreacted carbon dioxide and water in a stripper at a pressure substantially equal to said urea synthesis pressure while bringing said solution into contact or no contact with at least part of feed carbon dioxide and feed ammonia to separate said unreacted ammonia and said unreacted carbon dioxide as a gaseous mixture of ammonia, carbon dioxide and water, treating further the urea synthesis solution containing unseparated unreacted ammonia and unreacted carbon dioxide to obtain urea, separately introducing the gaseous mixture separated in said stripping zone into a condenser having a multi-tubular cooler to bring the mixture into contact with an absorption medium under cooling, thereby condensing said gseous mixture, and recycling the thus-obtained condensate to the urea synthesis column, characterized in that sites, that are to be in contact with said condensate, of the joint of a tube plate and cooling tubes in said condenser are enveloped with liquid ammonia or a solution rich in ammonia to prevent corrosion of said sites due to said condensate.

A urea synthesis apparatus comprising a urea synthesis column for reacting ammonia and carbon dioxide at a urea synthesis pressure and a urea synthesis temperature, a stripper for separating unreacted ammonia and carbon dioxide by heating a urea synthesis solution from said urea synthesis column at a pressure substantially equal to the urea synthesis pressure, a condenser having a multi-tubular cooler for condensing the unreacted ammonia and carbon dioxide from said stripper by bringing them into contact with an absorption medium, and a piping for introducing the condensate obtained in said condenser into the bottom part of the urea synthesis column, characterized in that said multi-tubular cooler has a baffle plate which covers sites, that are to be protected from corrosion, of the joints of a tube plate and cooling tubes and through which said cooling tubes penetrate with minute clearances held inbetween, and has an inlet nozzle or nozzles for supplying liquid ammonia into the space between said tube plate and said baffle plate.

BEST MODE FOR EFFECTING THE INVENTION

The condenser having a tubular cooler in the present invention is widely used as a vertical or horizontal type condenser in the technical field concerned.

The solution rich in ammonia that envelops the joints of a tube plate and cooling tubes and the solution rich in ammonia that occupies the space between a tube plate and a baffle plate are preferably a solution containing ammonia and ammonium carbamate, whose free ammonia content is 80 mol % or more.

Any method may be used to envelop sites, that are to be in contact with the condensate, of the joints of a tube plate and cooling tubes with liquid ammonia or a solution rich in ammonia. For example, sites, that are to be in contact with the condensate, of the joints of a tube plate and cooling tubes are covered with a baffle plate through which the cooling tubes penetrate with minute clearances held inbetween, and liquid ammonia or a solution rich in ammonia is fed to the space between the baffle plate and the tube plate, so that the space may be occupied with the liquid ammonia or solution rich in ammonia. The liquid ammonia supplied enters the condenser through the minute clearances between the tube plate and the cooling tubes and, together with an absorption medium, causes to condense and absorbs unreacted carbon dioxide and ammonia from the stripper. Another example employs no baffle plate but comprises feeding liquid ammonia or a solution rich in ammonia at a feed rate that sites, that are to be in contact with the condensate, of the joints of a tube plate and tubes are enveloped with the liquid ammonia or solution rich in ammonia to form curtains of the liquid ammonia or solution rich in ammonia and thereby to cut off contact of the sites with the corrosive condensate, so that the sites are protected from corrosion. A plural number of liquid ammonia feed points are preferred. Further, any method may be used as far as it can envelop sites, that are to be in contact with the condensate, of the joints of a tube plate and cooling tubes with liquid ammonia or a solution rich in ammonia.

The absorption medium to be fed to the condenser is preferably a recovery solution obtained by treating a urea synthesis solution, from which large part of unreacted ammonia and carbon dioxide has been separated in the stripper, at a medium and/or low pressure to separate substantially all of the remaining unreacted ammonia and carbon dioxide and causing water, aqueous ammonia or a urea solution to absorb the thus separated unreacted ammonia and carbon dioxide.

The present invention will be illustrated in detail with reference to the appended drawings as follows.

Figure 1:
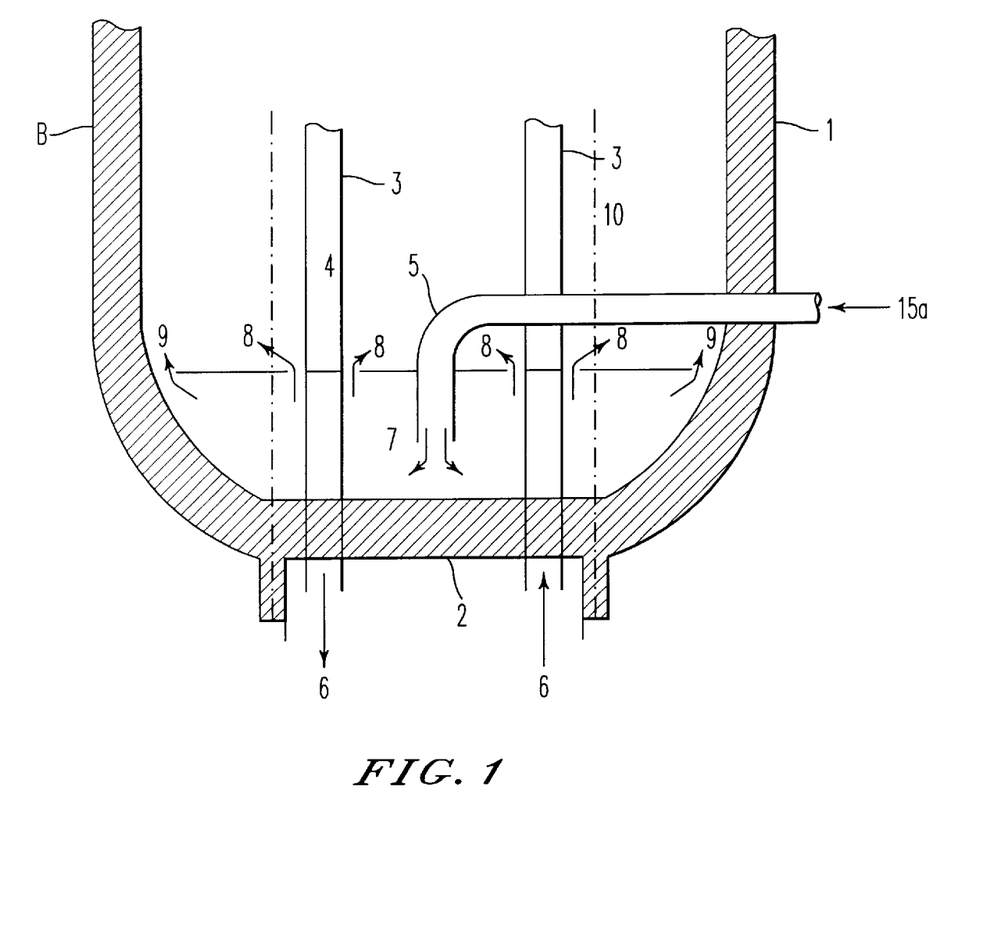
FIG. 1 is a partially enlarged view of a condenser B illustrating an embodiment of the present invention.
Figure 2:
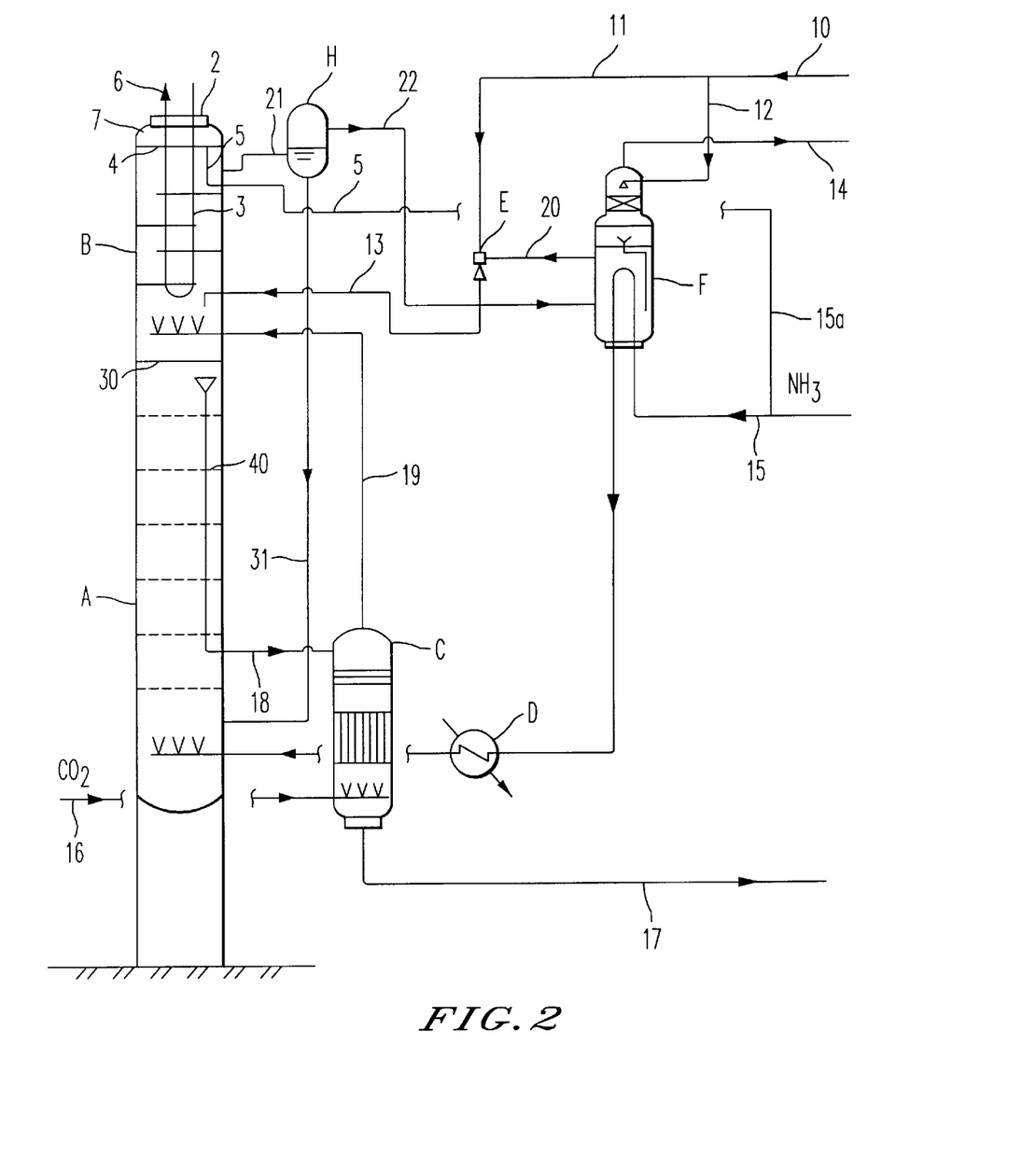
FIG. 2 is a flowsheet showing an embodiment of the present invention, in which a vertical condenser is employed.

FIG. 1 is a partially enlarged schematic view of a condenser B in the present invention, illustrating a part of a vertically installed condenser B as described in FIG. 2 by enlarging it schematically, the condenser B comprising a tube plate, a plurality of cooling tubes welded to the tube plate and selected, for example, from among hundreds to a thousand of tubes, and a baffle plate. Here, the tube plate 2 and the cooling tubes 3 are illustrated by referring to an example in which the plate and the tubes are welded together by internal bore butt welding. However, it goes without saying that the present invention is not limited to or by the example.

FIG. 2 is a process flow sheet illustrating an embodiment of the present invention where a vertical condenser is used, giving an example of urea synthesis process flows wherein the condensate is allowed to flow down by gravity from the condenser to a urea synthesis column, and the condenser whose tube plate and cooling tubes are protected from corrosion or cracking is installed vertically. The present invention will be described with reference to these drawings hereinbelow.

A part of a recovery solution, which has been formed by recovering unreacted ammonia and carbon dioxide as an aqueous solution of ammonium carbamate in a step not shown in FIG. 2, is introduced into a condenser B through lines 10, 11 and 13, while the rest is supplied to a scrubber F through a line 12. The above recovery solution supplied to the scrubber F absorbs ammonia and carbon dioxide in an inert gas, that contains small amounts of ammonia and carbon dioxide and is introduced into the scrubber F through a line 22, and is recycled again to the scrubber F. The recovery solution equivalent to the increment formed by absorbing the ammonia and carbon dioxide is pressurized by an ejector E via a line 20 and introduced into the condenser B via a line 13. Separately, the inert gas is discharged into the air from the scrubber F at the top.

A part of feed carbon dioxide is supplied to a stripper C through a line 16. Although not illustrated in the drawing, corrosion-preventive air is also supplied to the stripper C. A urea synthesis solution comprising urea, ammonium carbamate and ammonia is fed through a second down pipe 40 in the synthesis column A to the stripper C, where it undergoes stripping under heating by means of the carbon dioxide. Its operating conditions are usually a pressure of 140–200 bar and a temperature of 160–200° C.

Feed liquid ammonia is preheated, for example, to 70–90° C., introduced through a line 15, and further preheated through the scrubber F and a heat exchanger D, part of the ammonia being supplied to the bottom part of the synthesis column A, while the rest is fed to the condenser B through a branched line 5.

The aforesaid recovery solution sent to the vertical condenser B is brought into contact and mixed with a gaseous mixture comprising carbon dioxide, ammonia and inert gas, fed to the condenser B through a line 19 from the stripper C described below, thereby absorbing the carbon dioxide and ammonia. A part of feed liquid ammonia is introduced through a feed pipe 5 into a space 7 between a baffle plate 4 and a tube plate 2. The space 7 is filled with the liquid ammonia, which is caused to flow through clearances 8 between the baffle plate 4 and cooling tubes 3 and a clearance 9 between the baffle plate 4 and the shell 1 of the condenser, followed by mixing with a joined solution in the condensor. Here, the clearance 8 is from 0.1 mm to 0.5 mm from the viewpoint of precision of fabrication.

In the condenser B, the operating pressure is equivalent to that of the urea synthesis column, the N/C is 2.5–4.5, the H/C is 0.0–1.0, and the residence time is 10–30 minutes. The operating temperature is adjusted to be 150–200° C., preferably 160–200° C., more preferably 160–190° C. Since the condenser B is operated under these conditions, it can attain the same urea synthesis rate of 20–60% as in the past. In addition, as shown in Examples 1–4 below, it gives effects that troubles such as crack and corrosion of the weld joints of the cooling tubes 3 and the tube plate 2 do not grow.

Here, the condenser B is connected to a liquid-gas separator H for separating gas of the condenser B and the gas is separated in the liquid-gas separator H, the condenser B being filled with liquid.

In the urea synthesis column A, the feed liquid ammonia joins the condensate having flowed down by gravity through a first down pipe 31 from the condenser B. The resultant joined solution moves toward the top of the urea synthesis column A and is then sent to the stripper C through a second down pipe 40 provided in the column A and a line 18.

The operating pressure of the urea synthesis column A is selected to be 130–250 bar as in the conventional processes. The N/C is selected at 3.5–5.0, the H/C at 1.0 or less, and the residence time is selected to be 10–40 minutes. The operating temperature is controlled at 180–200° C., and under the foregoing conditions, the column A attains a urea synthesis rate of 60–75%.

Figure 3:
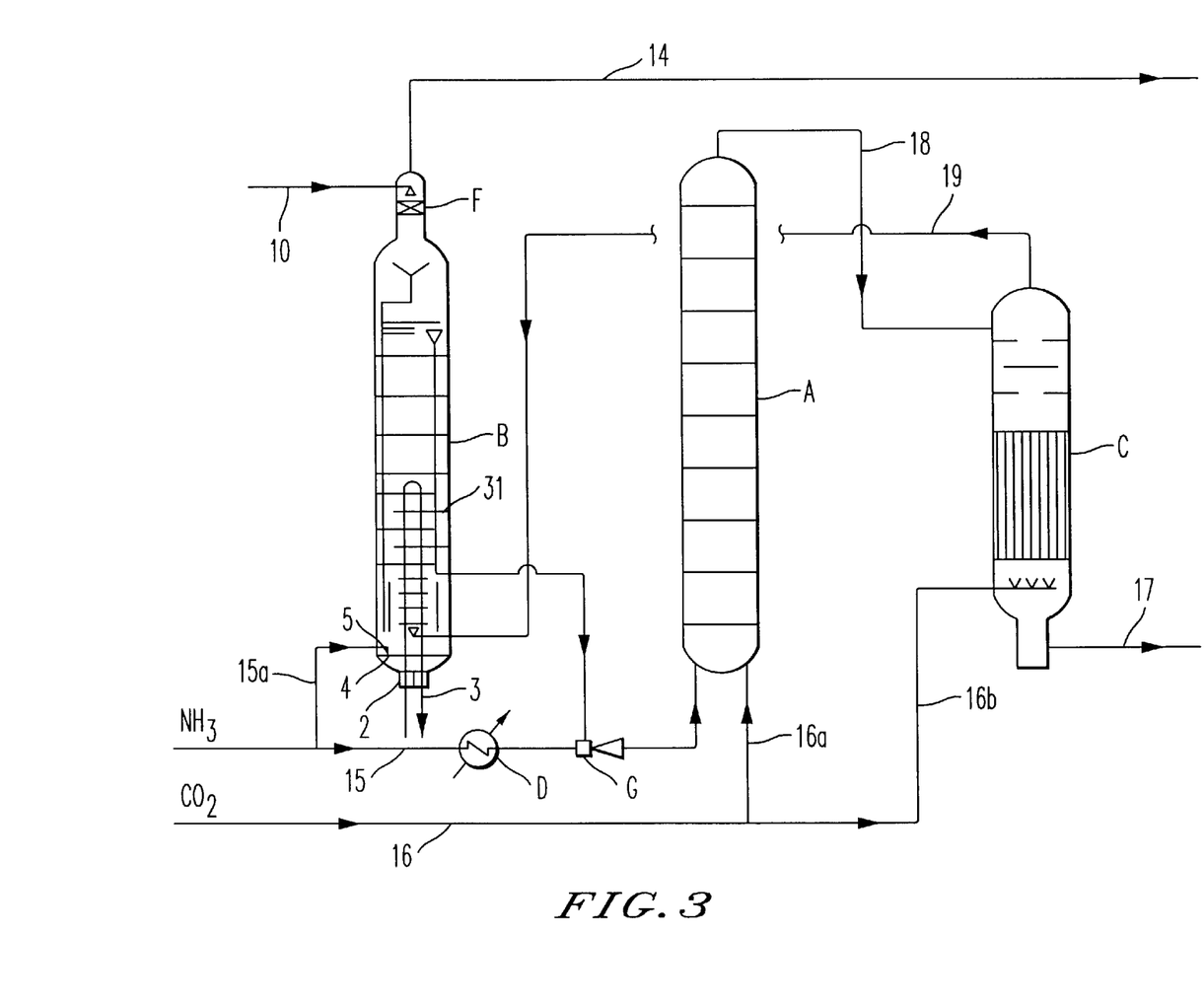
FIG. 3 is a flowsheet showing another embodiment of the present invention, in which a vertical condenser is employed.

Then, by referring to FIG. 3 showing a process flow of another embodiment which employs a vertical condenser of the present invention, a process is illustrated wherein an ejector G is used to introduce a joined solution in a condenser B into a urea synthesis column A. In FIG. 3, feed liquid ammonia is introduced through a line 15 into a heat-exchanger D under a pressure of 150–300 bar, where it is preheated to 100–200° C. and introduced into an ejector G as a driving fluid. The feed liquid ammonia is expanded through the ejector G so that the pressure difference between the delivery and suction pressures of the ejector may become 2–10 bar. In consequence, the joined solution supplied to the suction side of the ejector through a down pipe 31 in the vertical condenser B is sucked, pressurized, and introduced into the bottom part of the urea synthesis column A as a mixture with the driving fluid, i.e., the feed liquid ammonia. Of the feed carbon dioxide, carbon dioxide necessary for stripping unreacted ammonia and carbon dioxide is fed to the bottom part of the stripper C through lines 16 and 16b, and the rest is fed to the bottom part of the urea synthesis column A through a line 16a or to a low pressure decomposition step not shown in the drawing.

Part of the feed liquid ammonia is introduced through a feed pipe 5 into the aforesaid space 7 of the condenser via a line 15a branched from a line before the heat exchanger D. The feed liquid ammonia joins, at the bottom part of the condenser, a recovery solution fed from a line 10, which has absorbed unreacted ammonia and carbon dioxide while passing down through a scrubber F. The joined solution undergoes urea synthesis while going up through the vertical condenser B, and is then fed to the synthesis column A through the down pipe 31 by means of the ejector G. Part of the feed liquid ammonia introduced into the bottom part of the vertical condenser B through the feed pipe 5 via the line 15a may be supplied through a separately provided line which is not shown in the drawing.

Here, tube-expanded parts (tube rolls) of the tube plate 2 and the cooling tubes 3, sealweld joints of the tube-expanded parts and the tube plate or inner bore weld joints of the tube plate 2 and the cooling tubes 3 of the condenser located in the space 7 are filled with liquid ammonia or a solution rich in ammonia, and therefore are always maintained in an environment rich in ammonia. Accordingly, no corrosion takes place in the tube-expanded parts, weld joints and similar joints as shown in Example 3 below.

Regarding the operating conditions of the urea synthesis column A, a pressure of 130–250 bar, an N/C of 3.5–5.0, an H/C of 1.0 or less, a residence time of 10–40 minutes and a temperature of 180–200° C. are preferred.

As regards the operating conditions of the stripper C, a pressure of 130–250 bar, particularly 140–200 bar and a temperature of 160–200° C. are preferred.

From the bottom part of the stripper, a urea synthesis solution containing unseparated unreacted ammonia and unreacted carbon dioxide is drawn out through a line 17 and sent to a low pressure decomposition step where it is treated to obtain urea.

Details of the operation other than described above are practiced with reference to the process disclosed in the specification of Japanese Patent Application No. 234364/1997.

Figure 4:
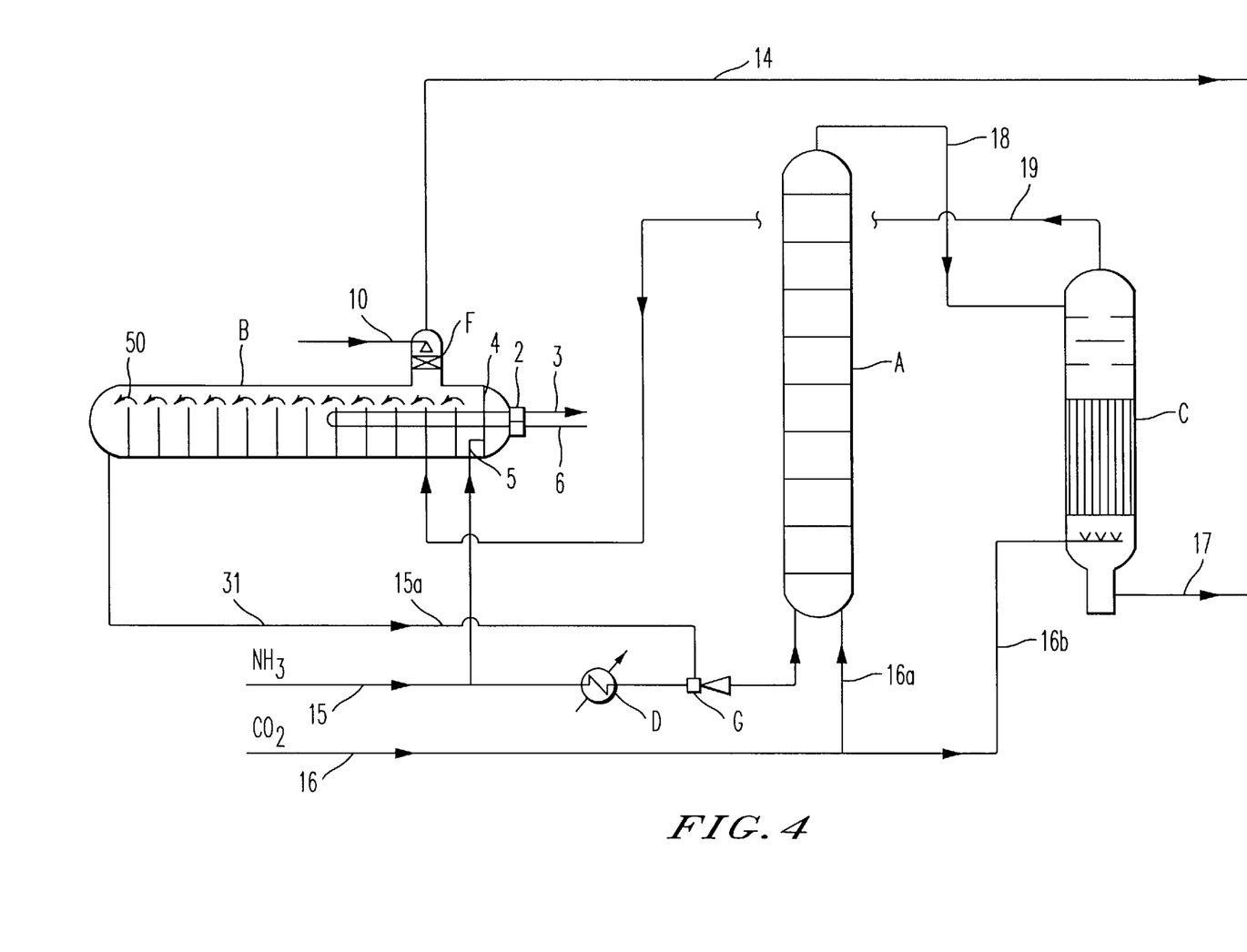
FIG. 4 is a flowsheet showing a further embodiment of the present invention, in which a horizontal condenser is employed.

An example using a horizontally placed condenser B is illustrated with reference to FIG. 4 which is a process flow diagram showing an embodiment in which a horizontal condenser of the present invention is employed. FIG. 4 is basically the same as FIG. 3 except that the vertically installed condenser B of FIG. 3 is placed horizontally, a plurality of baffle plates are provided vertically in the condenser B so that liquid is caused to flow along flow directions 50 over the baffle plates, and the height of the baffle plates is so determined that cooling tubes 3 may be immersed in liquid.

The present invention will be described more specifically by referring to the following examples. However, it should not be construed that the present invention is limited only to or by these examples.

In the following Examples 1–3 and Comparative Examples 1–3, all cooling tubes employed an austenitic 25Cr-22Ni-2Mo stainless steel as their material.

EXAMPLE 1

Urea was synthesized by using an apparatus with a daily production of 1,400 tons placed on the ground as shown in FIG. 2 in which a condenser B illustrated in FIG. 1 was placed vertically. A tube plate 2 and cooling tubes 3 were welded by internal bore butt welding and clearances 8 between a baffle plate 4 and cooling tubes 3 were 0.3 mm.

791 t/d of feed ammonia and 1,025 t/d of feed carbon dioxide were supplied through a line 15 and a line 16, respectively. The feed ammonia heated to 175° C. by steam condensate in a heat-exchanger D was fed to the bottom part of a synthesis column A through a line 15, while part of it was introduced through a branched line 15a and a feed pipe 5 into a space 7 of the condenser B shown in FIG. 1. The amount of ammonia through the line 15a was 401 t/d.

969 t/d of the feed carbon dioxide and about 17 t/d of corrosion-preventive air were supplied to the bottom part of a stripper C through the line 16, the rest of the feed carbon dioxide being supplied to a low pressure decomposition column not shown in the drawing. Separately, 1,314 t/d of a recovery solution fed through a line 10 as an absorption medium had the following composition and a temperature of 108° C. and was pressurized to 190 bar. The pressurized solution was divided into two, which were sent to a scrubber F and an ejector E through a line 12 and a line 11, respectively.

| | |
|---|---|
| urea | 0.4% |
| ammonia | 34.8% |
| carbon dioxide | 40.0% |
| water | 24.4% |

The recovery solution fed to the scrubber F was used to scrub inert gas in the packed layer, while the recovery solution fed to the ejector E was used to increase the pressure of a scrubber delivery solution (line 20) by the ejector E. The scrubber F was operated at 175 bar and 175° C. The scrubber delivery solution (line 20) and the ejector-driving recovery solution (line 11) were mixed in the ejector E and fed to the bottom part of the condenser B through a line 13.

A gaseous mixture comprising ammonia, carbon dioxide and water, separated in the stripper C, was sent to the condenser B through a line 19. The shellside of the condenser B was filled with a mixed solution comprising said recovery solution, ammonium carbamate formed by condensation and said feed liquid ammonia came out from the space 7 through clearances 8, and said gaseous mixture was absorbed in this solution. The heat of absorption was removed by a cooler 3. The condensate having absorbed the gaseous mixture stayed in the condenser for 15 minutes, was allowed to flow through a down pipe 31 by gravity, and then was sent to the bottom part of the urea synthesis column A. Inert gas was drawn out through a line 21 from the top part of the condenser B. The inert gas was subjected to liquid-gas separation in a liquid-gas separator H and fed through a line 22 to the scrubber F where ammonia and carbon dioxide contained therein were absorbed. The inert gas was discharged through a line 14.

The urea synthesis solution fed to the bottom part of the urea synthesis column A was mixed with said liquid ammonia from the line 15 and proceeded further with urea synthesis reaction while going up slowly through the synthesis column. The residence time for the reaction was 25 minutes.

The synthesis solution fed to the stripper C through a second down pipe 40 and a line 18 from the synthesis column A was heated in the stripper to decompose ammonium carbamate contained therein into ammonia and carbon dioxide. The stripper C was operated at a top temperature of 191° C., a bottom temperature of 179° C., and a pressure of 175 bar. The operating conditions and compositions in the foregoing equipments are shown in Table 1. After one year operation, corrosion and thickness reduction of the joints of the cooling tubes and the tube plate were inspected by means of ultrasonic flaw detection and eddy current examination. The results are shown in Table 5.

TABLE 1

|  | Example 1 | Comp. Ex. 1 |
| --- | --- | --- |
| Feed liquid ammonia (line 15) (t/d) | 792 | 792 |
| ditto (line 15a) (t/d) | 40 | 0 |
| Feed carbon dioxide (t/d) | 1025 | 1025 |
| Recovery Solution (t/d) | 1314 | 1314 |
| urea (%) | 0.4 | 0.4 |
| ammonia (%) | 34.8 | 34.8 |
| carbon dioxide (%) | 40.4 | 40.4 |
| water (%) | 24.4 | 24.4 |
| Condenser B |  |  |
| Pressure (bar) | 175 | 175 |
| temperature (° C.) | 185 | 185 |
| urea (%) | 21.1 | 21.1 |
| ammonia (%) | 34.3 | 34.3 |
| carbon dioxide (%) | 26.7 | 26.7 |
| water (%) | 17.9 | 17.9 |
| urea synthesis rate (%) | 42.6 | 42.6 |
| N/C | 2.85 | 2.85 |
| H/C | 0.67 | 0.67 |
| residence time (min.) | 15 | 15 |
| Synthesis Column A |  |  |
| pressure (bar) | 175 | 175 |
| temperature (° C.) | 185 | 185 |
| urea (%) | 31.8 | 31.8 |
| ammonia (%) | 36.8 | 36.8 |
| carbon dioxide (%) | 12.2 | 12.2 |
| water (%) | 19.2 | 19.2 |
| urea synthesis rate (%) | 65.7 | 65.7 |
| N/C | 4.0 | 4.0 |
| H/C | 0.67 | 0.67 |
| residence time (min.) | 25 | 25 |
| Stripper C (line 17) |  |  |
| urea (%) | 48.1 | 48.1 |
| ammonia (%) | 13.2 | 13.2 |
| carbon dioxide (%) | 13.7 | 13.7 |
| water (%) | 25.0 | 25.0 |
| Stripper C (line 16) |  |  |
| carbon dioxide (t/d) | 969 | 969 |

COMPARATIVE EXAMPLE 1

Urea synthesis was carried out in the same manner as in Example 1 except that the baffle plate 4 of Example 1 was removed and the amount of ammonia branched to the line 15a was changed from 40 t/d to 0 t/d. The operating conditions and compositions are described also in Table 1, and corrosion conditions of the joints of the tube plate and the cooling tubes in the condenser after one year operation are described in Table 5.

EXAMPLE 2

Urea was synthesized by using an apparatus with a daily production of 1,400 tone placed on the ground as shown in FIG. 3 in which a condenser B illustrated in FIG. 1 was placed vertically. A tube plate 2 and cooling tubes 3 were subjected to tube expansion and tube-end sealwelding, and clearances 8 between a baffle plate 4 and cooling tubes 3 were each 0.3 mm.

The operating conditions and liquid compositions of each equipment are shown in Table 2. Corrosion conditions of the joints of the tube plate and the cooling tubes after one year operation are described in Table 5.

TABLE 2

|  | Example 2 | Com. Ex. 2 |
| --- | --- | --- |
| Feed ammonia (line 15) (t/d) | 792 | 792 |
| ditto (line 15a) (t/d) | 40 | 0 |
| Feed carbon dioxide (t/d) | 1025 | 1025 |
| Recovery Solution (t/d) | 1314 | 1314 |
| urea (%) | 0.4 | 0.4 |
| ammonia (%) | 34.8 | 34.8 |
| carbon dioxide (%) | 40.4 | 40.4 |
| water (%) | 24.4 | 24.4 |
| Condenser B |  |  |
| Pressure (bar) top | 175 | 175 |
| ditto bottom | 176 | 176 |
| temperature (° C.) | 185 | 185 |
| urea (%) | 21.1 | 21.1 |
| ammonia (%) | 34.3 | 34.3 |
| carbon dioxide (%) | 26.7 | 26.7 |
| water (%) | 17.9 | 17.9 |
| urea synthesis rate (%) | 42.6 | 42.6 |
| N/C | 2.85 | 2.85 |
| H/C | 0.67 | 0.67 |
| residence time (min.) | 15 | 15 |
| Ejector |  |  |
| pressure (bar) suction | 176 | 176 |
| ditto delivery | 179 | 179 |
| Synthesis Column A |  |  |
| pressure (bar) top | 177 | 177 |
| temperature (° C.) | 185 | 185 |
| urea (%) | 31.8 | 31.8 |
| ammonia (%) | 36.8 | 36.8 |
| carbon dioxide (%) | 12.2 | 12.2 |
| water (%) | 19.2 | 19.2 |
| urea synthesis rate (%) | 65.7 | 65.7 |
| N/C | 4.0 | 4.0 |
| H/C | 0.67 | 0.67 |
| residence time (min.) | 25 | 25 |
| Stripper C (line 17) |  |  |
| pressure (bar) top | 177 | 177 |
| urea (%) | 48.1 | 48.1 |
| ammonia (%) | 13.2 | 13.2 |
| carbon dioxide (%) | 13.7 | 13.7 |
| water (%) | 25.0 | 25.0 |
| Stripper C (line 16b) |  |  |
| carbon dioxide (t/d) | 969 | 969 |

COMPARATIVE EXAMPLE 2

Urea was synthesized in the same manner as in Example 1 except that the baffle plate 4 of Example 2 was removed and the amount of ammonia branched was changed from 40 t/d to 0 t/d. The results are described also in Table 1. The operating conditions and corrosion conditions of the joints between the tube plate and the cooling tubes in the condenser are illustrated in Table 5.

EXAMPLE 3

Urea was synthesized by using an apparatus with a daily production of 1,400 tons placed on the ground as shown in FIG. 4 in which the condenser B illustrated in FIG. 1 was placed horizontally. A tube plate 2 and cooling tubes 3 were tube-expanded and sealwelded. Clearances 8 between a baffle plate 4 and cooling tubes 3 were each 0.3 mm.

The operating conditions and liquid compositions in each equipment are given in Table 3, and corrosion conditions of the joints of the tube plate and the cooling tubes after one year operation are described in Table 5.

TABLE 3

| | Example 3 | Comp. Ex. 3 |
|---|---|---|
| Feed ammonia (line 15) (t/d) | 792 | 792 |
| ditto (line 15a) (t/d) | 40 | 0 |
| Feed carbon dioxide (t/d) | 1025 | 1025 |
| Recovery Solution (t/d) | 1314 | 1314 |
| urea (%) | 0.4 | 0.4 |
| ammonia (%) | 34.8 | 34.8 |
| carbon dioxide (%) | 40.4 | 40.4 |
| water (%) | 24.4 | 24.4 |
| Condenser B | | |
| Pressure (bar) top | 175 | 175 |
| ditto bottom | 176 | 176 |
| temperature (° C.) | 185 | 185 |
| urea (%) | 21.1 | 21.1 |
| ammonia (%) | 34.3 | 34.3 |
| carbon dioxide (%) | 26.7 | 26.7 |
| water (%) | 17.9 | 17.9 |
| urea synthesis rate (%) | 42.6 | 42.6 |
| N/C | 2.85 | 2.85 |
| H/C | 0.67 | 0.67 |
| residence time (min.) | 15 | 15 |
| Ejector | | |
| pressure (bar) suction | 176 | 176 |
| ditto delivery | 179 | 179 |
| Synthesis Column A | | |
| pressure (bar) top | 177 | 177 |
| temperature (° C.) | 185 | 185 |
| urea (%) | 31.8 | 31.8 |
| arnmonia (%) | 36.8 | 36.8 |
| carbon dioxide (%) | 12.2 | 12.2 |
| water (%) | 19.2 | 19.2 |
| urea synthesis rate (%) | 65.7 | 65.7 |
| N/C | 4.0 | 4.0 |
| H/C | 0.67 | 0.67 |
| residence time (min.) | 25 | 25 |
| Stripper C (line 17) | | |
| pressure (bar) top | 177 | 177 |
| urea (%) | 48.1 | 48.1 |
| ammonia (%) | 13.2 | 13.2 |
| carbon dioxide (%) | 13.7 | 13.7 |
| water (%) | 25.0 | 25.0 |
| Stripper C (line 16b) | | |
| carbon dioxide (t/d) | 969 | 969 |

COMPARATIVE EXAMPLE 3

Urea was synthesized in the same manner as in Example 1 except that the baffle plate 4 of Example 2 was removed and the amount of ammonia branched was changed from 40 t/d to 0 t/d. The operating conditions and liquid composition in each equipment are given also in Table 3, and corrosion conditions of the joints between the tube plate and the cooling tubes in the condenser after one year operation are described in Table 5.

EXAMPLE 4

Urea was synthesized in a testing apparatus with a daily production of 10 t/d. The testing apparatus had a process flow as given in FIG. 3.

The condenser had ten tubes, of which six tubes were of internal bore welding, the rest four being joined to a tube plate by tube expansion (tube roll) and tube-end welding. The tube materials were (A) austenitic (25Cr-22Ni-2Mo) material and (B) two phase (25Cr-7Ni-3Mo) material which were respectively used in each half of the above-described groups of tubes.

The operating conditions and the material balance are shown in Table 4. The amount of ammonia supplied to the bottom tube plate was 12 kg/h. After about one year operation, the tube bundle was taken out, and the conditions of the joints were inspected from the shellside. Further, a tube of the bore welding and a tube of the tube expansion and tube-end welding for each material were cut at their joints and examined in detail on the presence of defects and corrosion conditions. The results did not show corrosion nor reduction in thickness to a measurable extent in both tubes A and B. Further, the tubes of tube expansion and tube-end welding had no observable crevice corrosion between the tubes and the tube plate. The results are given in Table 5.

TABLE 4

| | Example 4 | Comp. Ex. 4 |
|---|---|---|
| Feed ammonia (line 15) (t/d) | 5.66 | 5.66 |
| ditto (line 15a) (t/d) | 0.286 | 0 |
| Feed carbon dioxide (t/d) | 7.32 | 7.32 |
| Recovery Solution (t/d) | 9.39 | 9.39 |
| urea (%) | 0.4 | 0.4 |
| ammonia (%) | 34.8 | 34.8 |
| carbon dioxide (%) | 40.4 | 40.4 |
| water (%) | 24.4 | 24.4 |
| Condenser B | | |
| Pressure (bar) top | 175 | 175 |
| ditto bottom | 176 | 176 |
| temperature (° C.) | 185 | 185 |
| urea (%) | 21.1 | 21.1 |
| ammonia (%) | 34.3 | 34.3 |
| carbon dioxide (%) | 26.7 | 26.7 |
| water (%) | 17.9 | 17.9 |
| urea synthesis rate (%) | 42.6 | 42.6 |
| N/C | 2.85 | 2.85 |
| H/C | 0.67 | 0.67 |
| residence time (min.) | 15 | 15 |
| Ejector | | |
| pressure (bar) suction | 176 | 176 |
| ditto delivery | 179 | 179 |
| Synthesis Column A | | |
| pressure (bar) | 177 | 177 |
| temperature (° C.) | 185 | 185 |
| urea (%) | 31.8 | 31.8 |
| ammonia (%) | 36.8 | 36.8 |
| carbon dioxide (%) | 12.2 | 12.2 |
| water (%) | 19.2 | 19.2 |
| urea synthesis rate (%) | 65.7 | 65.7 |
| N/C | 4.0 | 4.0 |
| H/C | 0.67 | 0.67 |
| residence time (min.) | 25 | 25 |
| Stripper C (line 17) | | |
| pressure (bar) top | 177 | 177 |
| urea (%) | 48.1 | 48.1 |

TABLE 4-continued

|  | Example 4 | Comp. Ex. 4 |
|---|---|---|
| ammonia (%) | 13.2 | 13.2 |
| carbon dioxide(%) | 13.7 | 13.7 |
| water (%) | 25.0 | 25.0 |
| Stripper C (line 16b) | | |
| carbon dioxide (t/d) | 6.92 | 6.92 |

COMPARATIVE EXAMPLE 4

Urea was synthesized in the same apparatus and under the same operating conditions as in Example 4. However, the amount of ammonia fed to the bottom tube plate was 0 kg/h. The results are given in Table 5. The operating conditions and material balance are illustrated in Table 4. After about one year operation, both tubes A and B were observed to have reductions in thickness of 0.03–0.07 mm. The tubes of tube-end welding and tube expansion were found from the shellside to have crevice corrosion in the crevices between the tubes and the tube plate. The results are shown in Table 5.

In Comparative Example 4, it is necessary to make the tube thickness at the weld joint at least a required calculated thickness plus 1.4 mm in order to attain a life of twenty years where corrosion proceeds at the maximum corrosion rate measured. In the case of the tube-end welding plus tube expansion, crevice corrosion cannot be repaired so that dilution of the carbamate solution with ammonia is indispensable in the vicinity of the bottom tube plate.

TABLE 5

|  | Average reduction in thickness (mm/year) |
|---|---|
| Example 1 | no |
| Example 2 | no |
| Example 3 | no |
| Example 4 | no |
| Comp. Ex. 1 | 0.03–0.07 |
| Comp. Ex. 2 | 0.03–0.07 |
| Comp. Ex. 3 | 0.03–0.07 |
| Comp. Ex. 4 | 0.03–0.07 |

The improved process for synthesizing urea of the present invention and the apparatus therefor exhibit effects as described below.

(1) While preventing corrosion of the joints of a tube plate and cooling tubes in a condenser installed vertically or horizontally, the process condenses ammonia and carbon dioxide from a stripper in the shellside of the condenser, synthesizes concurrently urea from the condensate thus-obtained, and feeds the resultant solution from the condenser to a urea synthesis column to further synthesize urea. Consequently, no trouble is caused in the cooling tubes.

(2) Since the process carries out condensation and urea synthesis while preventing corrosion of the joints between the tube plate and the cooling tubes in the condenser, no trouble is caused in the cooling tubes.

(3) Since no trouble is caused in the cooling tubes and similar devices, a great deal of time, expenses and energy can be reduced, which are required for repairs such as rewelding that have hitherto been necessary to cope with the trouble.

(4) Since no trouble is caused in the cooling tubes and similar devices, interruption of operation which is to follow the trouble does not occur and stable continuous operation became possible. As a result, a stable production rate can readily be maintained.

(5) Since no trouble is caused in the cooling tubes and similar devices, time and labor for periodic maintenance and inspection can be reduced significantly.

What is claimed is:

1. A urea synthesis process comprising reacting ammonia with carbon dioxide at a urea synthesis temperature and a urea synthesis pressure in a urea synthesis column, heating the resultant urea synthesis solution comprising urea, unreacted ammonia, unreacted carbon dioxide and water in a stripper at a pressure substantially equal to the urea synthesis pressure while bringing said solution into contact or no contact with at least part of feed carbon dioxide or feed ammonia to separate said unreacted ammonia and said unreacted carbon dioxide as a gaseous mixture of ammonia, carbon dioxide and water, treating further the urea synthesis solution containing unseparated unreacted ammonia and unreacted carbon dioxide to obtain urea, separately introducing the gaseous mixture separated in said stripper into a condenser having a tubular cooler to bring the mixture into contact with an absorption medium under cooling, thereby condensing said gaseous mixture, and recycling the thus-obtained condensate to the urea synthesis column, wherein sites, that are to be in contact with said condensate, of the joints of cooling tubes and a tube plate in said condenser are enveloped with liquid ammonia or a solution rich in ammonia to prevent corrosion of said sites due to said condensate.

2. The process as claimed in claim 1, wherein said sites of the joints of the tube plate and the cooling tubes are covered with a baffle plate through which said tubes penetrate with minute clearances held inbetween, and at least part of feed liquid ammonia is supplied to the space between said tube plate and said baffle plate so that said space is filled with liquid ammonia or a solution rich in ammonia.

3. The process as claimed in claim 1, wherein said condenser is installed on or above said urea synthesis column, and said condensate is allowed to flow down by gravity through a piping connecting the top part of said condenser with the bottom part of said urea synthesis column.

4. The process as claimed in claim 1, wherein said condensate is pressurized by means of an ejector driven by feed liquid ammonia so that it is recycled to the urea synthesis column.

5. A urea synthesis apparatus comprising a urea synthesis column for reacting ammonia and carbon dioxide at a urea synthesis pressure and a urea synthesis temperature, a stripper for separating unreacted ammonia and carbon dioxide by heating the urea synthesis solution from said urea synthesis column at a pressure substantially equal to the urea synthesis pressure, a condenser having a multi-tubular cooler for condensing the unreacted ammonia and carbon dioxide from said stripper by bringing them into contact with an absorption medium, and a piping for introducing the condensate obtained in said condenser into the bottom part of the urea synthesis column, wherein said multi-tubular cooler has a baffle plate which covers, sites, that are to be protected from corrosion, of the joints of a tube plate and cooling tubes and through which said cooling tubes penetrate with minute clearances held inbetween, and has an inlet nozzle or nozzles for supplying liquid ammonia to the space between said tube plate and said baffle plate.

6. The apparatus as claimed in claim 5, wherein said stripper has, at the bottom part thereof, an inlet nozzle or nozzles for supplying at least part of feed ammonia or carbon dioxide as a stripping agent.

7. The apparatus as claimed in claim 5, wherein said condenser is installed on or above said urea synthesis column, and said piping from said condenser to said urea synthesis column is for allowing a condensate from said condenser to flow down by gravity to the bottom part of said urea synthesis column.

8. The apparatus as claimed in claim 5, wherein the piping for introducing said condensate from said condenser to said urea synthesis column has an ejector for pressurizing said condensate, driven by feed liquid ammonia.

* * * * *